United States Patent
Roziev et al.

(10) Patent No.: US 9,949,961 B2
(45) Date of Patent: Apr. 24, 2018

(54) AGENT FOR THE PROPHYLAXIS AND/OR TREATMENT OF NEOPLASTIC DISEASES

(71) Applicants: Rahimdzhan Roziev, Obninsk (RU); Anna Ya. Goncharova, Obninsk (RU); Kenes T. Erimbetov, Borovsk (RU); Vladimir Podgorodnichenko, Obninsk (RU); Victor Khomichenok, Obninsk (RU); Natal'ja Novozhilova, Obninsk (RU)

(72) Inventors: Rahimdzhan Roziev, Obninsk (RU); Anna Ya. Goncharova, Obninsk (RU); Kenes T. Erimbetov, Borovsk (RU); Vladimir Podgorodnichenko, Obninsk (RU); Victor Khomichenok, Obninsk (RU); Natal'ja Novozhilova, Obninsk (RU)

( * ) Notice: Subject to any disclaimer, the term of this patent is extended or adjusted under 35 U.S.C. 154(b) by 0 days.

(21) Appl. No.: 14/775,698

(22) PCT Filed: Mar. 12, 2014

(86) PCT No.: PCT/IB2014/059659
§ 371 (c)(1),
(2) Date: Sep. 13, 2015

(87) PCT Pub. No.: WO2014/141082
PCT Pub. Date: Sep. 18, 2014

(65) Prior Publication Data
US 2016/0038472 A1    Feb. 11, 2016

(30) Foreign Application Priority Data

Mar. 14, 2013  (RU) ................... 2013111415
Mar. 14, 2013  (RU) ................... 2013111416

(51) Int. Cl.
| | | |
|---|---|---|
| C07D 417/06 | (2006.01) |
| C07D 277/36 | (2006.01) |
| A61K 31/4436 | (2006.01) |
| A61K 31/426 | (2006.01) |
| A61K 31/4439 | (2006.01) |

(52) U.S. Cl.
CPC ........ *A61K 31/4436* (2013.01); *A61K 31/426* (2013.01); *A61K 31/4439* (2013.01); *C07D 277/36* (2013.01); *C07D 417/06* (2013.01)

(58) Field of Classification Search
None
See application file for complete search history.

(56) References Cited

U.S. PATENT DOCUMENTS

| | | |
|---|---|---|
| 5,968,505 A | 10/1999 | Fahey et al. |
| 5,968,567 A | 10/1999 | Fahey et al. |
| 2003/0195238 A1* | 10/2003 | Gil ............... C07C 49/395 514/362 |

FOREIGN PATENT DOCUMENTS

| | | |
|---|---|---|
| RU | 2391342 C2 | 6/2010 |
| RU | 2405782 C2 | 12/2010 |
| RU | 2010129238 A | 1/2012 |
| SU | 119529 A1 | 11/1958 |

OTHER PUBLICATIONS

Martin & Rieche, 6(1) Monatsberichte Der Deutschen Akademie Der Wissenschaften Zu Berlin 22-32 (1964) (CAS Abstract).*
C. Ernst Redemann; Roland N. Icke; Gordon A. Alles (1955), "Rhodanine", Org. Synth.; Coll. vol. 3: 763.
Johannes S. Buck and Clifford S. Leonard "Rhodanines I. derivates of β-phenylethylamines", J. Am. Chem. Soc., v.53, issue 7, pp. 2688-2692, 1931.
Translation of the ISR (PCTIB2014059659).
The Written Opinion of the International Search Authority (PCTIB2014059659).
Initial Publication with ISR (PCTIB2014059659).

* cited by examiner

*Primary Examiner* — Timothy R Rozof

(57) ABSTRACT

The invention relates to a novel agent in the form of rhodanine derivatives, which has prophylactic, antiproliferative and antimetastatic activity. Said agent can find use in medicine and pharmacology for the prophylaxis and/or treatment of neoplastic diseases of variable localization.

1 Claim, No Drawings

AGENT FOR THE PROPHYLAXIS AND/OR TREATMENT OF NEOPLASTIC DISEASES

The invention refers to a novel agent representing derivates which has prophylactic, anti-proliferative and anti-metastatic activity. The specified agent may be applicable in medicine and pharmacology for prophylaxis and/or treatment of neoplastic diseases of various localization.

Prophylaxis of diseases including neoplastic ones is the main trend of modern medicine. Currently, extensive knowledge has been accumulated concerning possible prevention of neoplastic diseases with various substances contained in vegetable food products. The sound evidence has been presented obtained in numerous epidemiologic, studies showing that incidence rates of king, gastric, gastrointestinal cancer including colon cancer, ovarian and prostate cancer have been significantly reduced in the population residing in areas with high consumption of cruciferous vegetables. The experimental studies with various experimental models have established that formation of the abovementioned neoplasms is inhibited by various isothiocyanates (ITC) in cruciferous vegetables. The preventive effect of ITCs was related with their ability to modulate enzymes of the first and second phase of xenobiotic metabolism. As it is known, most chemical carcinogens are inactive and become active getting into animal body, are biotransformed under the effect of enzymes of the first phase of xenobiotic metabolism, mainly cytochrome P450 enzymes. Transformed chemical carcinogens acquire ability to interact with normal cell DNA which may result in malignant cell transformation. ITCs inhibit activity of the enzymes of the first phase of xenobiotic metabolism and suppress reaction of carcinogens with DNA. Activating enzymes of the second phase of xenobiotic metabolism, ITCs promote more rapid elimination of carcinogens from the body.

The property of ITC contained in vegetable products to prevent development of cancer diseases is implemented only partially if used by humans. It may be related with their irregular, insufficient or excessive consumption. Moreover, there is a certain threat of consumption of excessive ITC amounts related with the filet that ITC are weak mutagens, and their ability to induce malignant tumors in animals was shown in individual model experiments.

High toxicity inherent to conventional chemotherapy products prevents higher efficacy which may be achieved in treatment of cancer diseases. To improve results of malignant neoplasm treatment, new highly effective drug products with low toxicity are required. Such products may be artificially produced as a result of chemical synthesis or found among natural substances of vegetable or animal origin. Edible plants refer to objects of vegetable origin prospective for search of the substances which are able to suppress tumor growth, so as in the case, it is certainly ensured that the plant-derived substances will not cause serious adverse effects. Cruciferous vegetables belong to compounds prospective for search which have anti-neoplastic activity and are applicable for development of appropriate drug products. In the areas in which people consume a great amount of cruciferous vegetables, incidence rates of individual cancers are significantly lower. It is known that cruciferous vegetables contain a large amount of glucosinilates from which several isothiocyanates are enzymatically formed if plant integrity is impaired. As it is established, natural isothiocyanates in systems in vitro inhibit cell proliferation in various degree suppressing cell origin by cell type and, moreover, induce apoptosis of tumor cells.

It is prospective to use purified ITC for prevention or treatment of cancer diseases which are easily administered, and dosing of which does not depend on consumption of definite types of vegetables which significantly facilitates prevention or treatment. However, the fact that ITCs, as a rule, are oily liquids with harsh smell having a strong irritant, effect on mucosa, prevents their use.

ITCs are contained in plants as thioglycoside conjugates called glucosinilates with a weak smell which do not have mucosal irritant effect and are gradually hydrolyzed under effect of enzymes with ITC release. Nowadays, over 120 natural glucosinilates are known. The role of phenyl ethylthiocyanates (PETCC) in prevention of human cancer is most well-known.

The known anti-neoplastic agents of plant origin which are metabolic precursor isothiocyanates, are described, e.g. U.S. Pat. No. 5,968,505 or U.S. Pat. No. 5,968,567. Such agents reduce carcinogen levels in animals.

However, the use of natural isothiocyanates is limited with their low concentration in plant raw materials, as well as they are not to be stored for a long time.

C. Ernst Redemann, Roland N. Icke; Gordon A. Niles (1955), "Rhodanine", Org. Synth.; Coll. Vol. 3: 763 describes the production method of unsubstituted rhodanine with interaction of ammonium dithiocarbamate and sodium chloroacetate, with subsequent cyclization of resulting dithiocarbamate salt of acetic acid. The administration of the specified compound is not stated. The publication of Johannes S. Buck and Clifford S. Leonard "Rhodanines I. derivates of β-phenylethylamines", J. Am. Chem. Soc., v. 53, issue 7, pp. 2688-2692, 1931 describes the production of the formula compound I at X=CH.

RU2405782C2 describes 5-quinazoline-6-ylmethylen-2-thyoxo thiazolidinone-4-one as intermediate manufacturing product of 5-[1-quinazoline-6-ylmeth-(Z)-ilyden]-2-substituted amino]thyazol-4-one intended for cancer treatment, especially solid tumors, more preferably lung cancer, breast cancer, colon cancer and prostate cancer.

Application for US 2003/0195238 A1, 2003, formerly known substance 3-(2-phenylethl)-2-thyoxo-4-thiazolidinone) reveals anti-proliferative effect on neuroblastoma N2A cell culture.

The aim of the present invention is to search for new agents for prophylaxis and/or treatment of neoplastic diseases of various localization which simultaneously have the following characteristics:
  have anti-proliferative and anti-metastatic effects,
  have enhanced organoleptic properties,
  preserve high anti-cancer and anti-metastatic activity,
  preserve stability in storage and, consequently, have enhanced technological properties for production of the dosage form.

The invention refers to the new agent with prophylactic, anti-proliferative and anti-metastatic activity for prevention and treatment of neoplastic diseases which represents rhodanine derivates with the following structural formula (I):

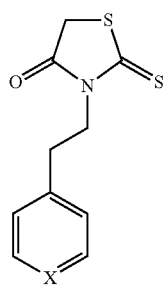

where X=CH (Product 1) or N (Product 2)

The formula compounds (I) are derived via cyclization of 2-phenylethyl dithiocarbamate of acetic acid or (2-pyridine-4-yl-ethylcarbomoylsulfanyl)-acetic acid, respectively, by the method described in C. Ernst Redemann: Roland N. Icke: Gordon A. Alles (1955), "Rhodanine", Org. Synth.; Coll. Vol. 3: 763.

In contrast to the previously known compounds, the invention compounds do not have unpleasant smell, the resulting compounds represent a powder with a weak smell of cruciferous plants which are easily pelleted. The resulting compounds are stable in storage and were tested for prophylactic and anti-neoplastic activity. Along with prophylactic properties inherent to glucosinilates, the proposed rhodanine derivates have additional properties as they contain residual thioglycolic acid which bind highly toxic water-soluble salts of heavy metals, and in accordance with the invention, may be also used for elimination of heavy metal ions, as well as for prevention of exposure of adverse factors in people residing in ecologically contaminated districts, for prophylaxis and neutralization of exposure of hazardous substances in industrial conditions, especially iron and steel industry. The use of the invention compound showing anti-proliferative and anti-metastatic effects, for treatment of anti-neoplastic diseases has not been known.

Proof of Prophylactic Effect

The efficacy of preventive effects of Products 1 and 2 in relation to hepatic neoplasms was shown in the experiment on male Wistar rats which were intraperitoneally administered with chemical carcinogen-N-diethyl nitrosamine (DENA) (Nitrosodiethylamin (N—N)). The nature of the invention is explained with the execution example.

EXAMPLE 1

To solve the task, 3 groups of male Wistar rats weighing 150-200 g were formed, 16 in each. Rats of the control group were administered intraperitoneally with DENA in dose 30 mg/kg/week. The dosage was administered in 2 doses: Monday and Thursday. The animals of test groups were similarly administered with DENA. Rats of test groups took drinking water in addition to Products 1 and 2 assuming that they took 25 mg/kg of body weight/day with water. The animals started taking the products 3 weeks prior administration of N-diethyl nitrosamine to develop protective background in animal body and subsequently for 2.5 months.

During the experiment, weight of rats was controlled. After autopsy of animals, liver was weighted, tumors were visually counted on its surface and photographed.

TABLE 1

Number of hepatic neoplasms in rats

| Parameters | Groups | | |
|---|---|---|---|
| | Control | Product 1 | Product 2 |
| Number of animals in group | 16 | 16 | 16 |
| Weight of rats, g | 149.1 ± 2.95 | 146.4 ± 3.57 | 145.9 ± 1.26 |
| Weight of liver, g | 7.9 ± 0.32 | 7.4 ± 0.19 | 7.0 ± 0.15 |
| Number of animals with induced tumors | 16 | 15 | 15 |
| Number of hepatic tumors | 66.7 ± 7.06 | 15.1 ± 2.88* | 16.6 ± 3.12* |

Remark:
*$P < 0.01$

The study results have shown that Products 1 and 2 have preventive effect in relation to hepatic tumors. So the administration of products 1 and 2 in dose 25 mg/kg a day allowed to decrease the number of tumors in 4.0-4.4 times in comparison with control group (group 1: animals took only carcinogen). The use of the Student's test to compare experimental groups with control showed significant difference ($P<0.01$).

So the products have preventive effect in relation to hepatic rats having chemical carcinogenesis.

The efficacy of anti-neoplastic (anti-proliferative) and anti-metastatic properties of products 1 and 2 was shown in the experiment on male mice $F_1$ (CBA×CS7B1/6) with Lewis carcinoma implanted to the paw following intragastric administration in two doses: 5 mg/kg and 25 mg/kg for 3 weeks immediately after implantation and within 1 week prior tumor transplantation.

The nature of the invention is explained by the execution example.

EXAMPLE 2

Test system. To examine anti-neoplastic (anti-proliferative) and anti-metastatic properties of products 1 and 2, 120 hybrid male mice of the first generation CBA×C57B1/15 were used: each group of 10-12 mice. Lewis carcinoma was implanted to a hind paw, in the amount ~$10^6$ cells (~0.2 cm$^3$) Doses and dosing schemes for products 1 and 2. Route of the product administration—per os provided addition of products 1 and 2 to drinking water which was given to animals. Products 1 and 2 were added to drinking water by two schemes: within 3 weeks immediately after implantation and within 4 weeks with the dosing started prior implantation. Experimental groups, doses and terms of administration were provided in table 2.

TABLE 2

Experimental groups

| # | Groups | Product scheme administration | Number of animals |
|---|---|---|---|
| 1 | Control | — | 10 |
| | | Product 1 | |
| 2 | 5 mg/kg | Prior and after tumor implantation (scheme 1) | 10-12 |
| 3 | | Only after tumor implantation (scheme 2) | 10-12 |
| 4 | 25 mg/kg | Prior and after tumor implantation (scheme 1) | 10-12 |
| 5 | | Only after tumor implantation (scheme 2) | 10-12 |

TABLE 2-continued

| # | Groups | Product scheme administration | Number of animals |
|---|--------|-------------------------------|-------------------|
|   |        | Product 2                     |                   |
| 6 | 5 mg/kg | Prior and after tumor implantation (scheme 1) | 10-12 |
| 7 |        | Only after tumor implantation (scheme 2) | 10-12 |
| 8 | 25 mg/kg | Prior and after tumor implantation (scheme 1) | 10-12 |
| 9 |        | Only alter tumor implantation (scheme 2) | 10-12 |

Anti-neoplastic (anti-proliferative) and anti-metastatic activity of products 1 and 2 was assessed based on change of tumor volume and number of lung metastases. The number of metastases was assessed on day 21 after tumor implantation (day 28 after the administration of products 1 and 2 by the 1-st scheme). For that, lungs were withdrawn in animals decapitated under anesthesia and transferred to Bouin's fluid. Metastases were visually counted. The volume of neoplasm was assessed by ellipsoid equation (1). Measurement terms: day 7, 14 and 21 after implantation.

$$V = \pi \cdot \frac{d_1 \cdot d_2 \cdot d_3}{6} \quad (1)$$

where: $d_1$, $d_2$, $d_3$—mutually perpendicular tumor sizes.

The obtained data have shown the administration of products 1 and 2 to animals significantly reduces tumor volume in comparison with control group (tabl. 3) already after 7 days. Significant differences from control were obtained for all experimental animals including the scheme providing minimum consumption of products 1 and 2 by animals: start of dosing—after implantation, dos—5 mg/kg.

Anti-neoplastic activity of products 1 and 2 tended to depend on dosing scheme and dose. As well as the increase of product 1 and 2 dose resulted in decrease of tumor volume on 23-24% if doses prior and after tumor implantation and 19-21% if dosed only after tumor implantation. The product of the treatment course with products 1 and 2 through drinking water up to four weeks, starting one week prior tumor implantation, resulted in decrease of tumor volume on 13-14% in dose 5 mg/kg and 15-16% in dose 25 mg/kg.

The analysis of number of lung metastases showed significant difference from control only for groups 5 and 9 start of administration in dose 25 mg/kg immediately after implantation (tab.4).

TABLE 3

Change of tumor volume in animals depending on the product dose and dosing scheme[1]

|   | Dose and dosing scheme | | Day after the product dosing | | |
|---|---|---|---|---|---|
|   |   |   | 1 | 7 | 15 |
| 1 | Control | | $45 \pm 15$ | $959 \pm 131$ | $2973 \pm 338$ |
|   | | Product 1 | | | |
| 2 | 5 mg/kg | Prior and after implantation | $40 \pm 15$ | $715 \pm 103$ | $1597 \pm 133$ ($P < 0.01$)[2] |
| 3 |         | After implantation | $52 \pm 17$ | $708 \pm 86$ | $1826 \pm 196$ ($P < 0.05$) |
| 4 | 25 mg/kg | Prior and after implantation | $101 \pm 29$ | $671 \pm 104$ | $1225 \pm 214$ ($P < 0.01$) |
| 5 |          | After implantation | $60 \pm 19$ | $812 \pm 153$ | $1437 \pm 325$ ($P < 0.01$) |
|   | | Product 2 | | | |
| 6 | 5 mg/kg | Prior and after implantation | $39 \pm 13$ | $706 \pm 99$ | $1588 \pm 127$ ($P < 0.01$)[3] |
| 7 |         | After implantation | $49 \pm 15$ | $702 \pm 92$ | $1806 \pm 203$ ($P < 0.05$) |
| 8 | 25 mg/kg | Prior and after implantationtion | $98 \pm 95$ | $650 \pm 97$ | $1204 \pm 226$ ($P < 0.01$) |
| 9 |          | After implantation | $70 \pm 14$ | $827 \pm 140$ | $1459 \pm 299$ ($P < 0.01$) |

Remark:
[1] Here and hereinafter tumor volume is stated in mm³, its size in mm, body weight in grams, error of the mean is given after sign ±.
[2] By Tukey's test in comparison with control group.
[3] By Student's test in comparison with control group.

TABLE 4

Number of lung metastases depending on the product dose and dosing scheme

|   | Dose and dosing scheme | | |
|---|---|---|---|
| 1 | Control | | $42.7 \pm 6.0$ |
|   | | Product 1 | |
| 2 | 5 mg/kg | Prior and after implantation | $42.2 \pm 7.1$ |
| 3 |         | After implantation | $32.8 \pm 8.1$ |
| 4 | 25 mg/kg | Prior and after implantation | $33.1 \pm 9.1$ |
| 5 |          | After implantation | $20.3 \pm 4.2$ ($P < 0.01$)[2] |
|   | | Product 2 | |
| 6 | 5 mg/kg | Prior and after implantation | $43.4 \pm 6.5$ |
| 7 |         | After implantation | $33.3 \pm 7.8$ |

TABLE 4-continued

Number of lung metastases depending on the product dose and dosing scheme

| | | Dose and dosing scheme | |
|---|---|---|---|
| 8 | 25 mg/kg | Prior and after implantation | 34.2 ± 8.9 |
| 9 | | After implantation | 19.0 ± 5.1 (P < 0.01)[3] |

Remark:
[1]Here and hereinafter tumor volume is stated in mm$^3$, its size in mm, body weight in grams, error of the mean is given after sign ±.
[2]By Tukey's test in comparison with control group.
[3]By Student's test in comparison with control group.

As a result of the study, it is established that products 1 and 2 are able to inhibit growth of Lewis carcinoma in mice. The inhibition is dose-related. Following administration of products 1 and 2 in dose 25 mg/kg of animal body weight, inhibition of tumor is more marked than in administration of dose 5 mg/kg. But following administration of both doses, tumor sizes differ significantly from the sizes in control group of annuals. Preliminary administration of products 1 and 2 for 1 week prior tumor inoculation increases the product efficacy. The study of product 1 and 2 effects on metastasis allows to establish that the products in dose 25 mg/kg of animal body weight significantly decreases the number of lung metastases following administration after tumor implantation. The number of lung metastases tends to be decreased following administration of products 1 and 2 in dose 5 mg/kg of body weight.

The invention claimed is:
1. Method of treating neoplastic diseases of the liver and hepatic neoplasm comprising the rhodanine derivative of the following structural formula:

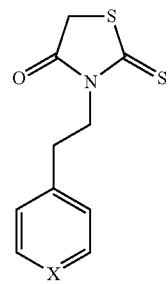

where X=N or CH.

* * * * *